United States Patent [19]

Kirsch

[11] Plant 4,880

[45] Aug. 24, 1982

[54] LILY NAMED ESCORT

[75] Inventor: Ted T. Kirsch, Myrtle Point, Oreg.

[73] Assignee: Sun Valley Bulb Farms, Inc., Myrtle Point, Oreg.

[21] Appl. No.: 215,535

[22] Filed: Dec. 11, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct variety of Oriental Hybrid lily plant of the Parkmannis type, particularly distinguished by its large, brilliant, purplish-red, heavily spotted flowers which are borne on short, stiff stems and strong, upwardly-extending pedicels, usually with one bud or flower on each pedicel, and by its very wide, oval, dark green, glossy and relatively disease-resistant foliage. Its short and squatty, compact growth habit makes it an ideal plant for pot culture.

2 Drawing Figures

BACKGROUND OF THE NEW PLANT

This new variety of lily plant originated as a seedling of unknown parentage growing among similar plants at my nursery in Arcata, Calif. The very large, brilliantly colored, outwardly facing flowers, dark green glossy foliage, and short, compact growth habit prompted me to select this plant for propagation, which I did asexually, with the result that I found this plant to have advantageous and distinctive characteristics which make the plant a valuable addition to the commercial field of lily pot plant culture. Propagation of this new lily plant at Arcata, Calif., through successive generations by means of scales and tissue culture, has shown that the distinctive characteristics of this plant hold true from generation to generation and appear to be firmly fixed.

DESCRIPTION OF THE DRAWING

This new variety of lily plant is illustrated by the accompanying full color photographic drawing which shows a full grown blooming plant in the upper view and a close-up of several blooms in the lower view, the color rendition being as nearly true as can be reasonably obtained by conventional photographic procedures.

DESCRIPTION OF THE NEW PLANT

The following is a detailed description of my new variety of lily based upon observations of greenhouse grown plants at Arcata, Calif., in the spring of 1980, with color designations according to the R.H.S. Colour Chart published by The Royal Horticultural Society of London, England.

THE PLANT

Origin: Seedling.

Parentage: Unknown.

Classification: Oriental Hybrid — Parkmannis type.

Form: Tall single stem from each bulb.

Height: 1 to 2 feet at maturity.

Growth: Vigorous, short and squatty, with outwardly-facing flowers.

Cane size: Stems grow from a $\frac{1}{8}$ inch base diameter when the plant is at a height of 1 foot to about $\frac{3}{8}$ inch base diameter when the plant is at a height of about 2 feet.

Foliage:

*Leaves at the flower cluster.*—Three in number, two at the base of each pedicel, 3 inches long and 1 to 2 inches wide, and one approximately $\frac{1}{2}$ inch from the flower bud, $3\frac{1}{2}$ inches long and $1\frac{1}{2}$ inches wide.

*Shape of leaf.*—Ovate, with cuspidate apex.

*Texture.*—Leathery.

*Aspect.*—Smooth.

*Ribs and veins.*—Distinct longitudinal veins from base to tip.

Bulblets (underground):

*Occurrence.*—One to three on each healthy, normal plant at digging time.

Bulbs:

*Size.*—From 6 inches to 10 inches in circumference, depending upon age.

*Color.*—White, with yellow and pink overtones. As the bulbs become larger and older, the overtones of yellow and pink become more and more prominent.

THE BUD

Form: Lanceolate, with acuminate apex.

Size: Averaging about $4\frac{1}{2}$ to $5\frac{1}{2}$ inches long and 1 inch to $1\frac{1}{2}$ inches in diameter.

Number: Usually one on each pedicel, with one to eight buds on a plant according to culture and bulb size.

Opening rate: Normal; buds open successively from the lowermost bud to the top bud, which is the last to open.

Color: Reddish-pink at the tip of the bud fading to a whitish-pink at the base when the sepals are about to divide and petals begin to unfurl.

Surface texture: Rugose and leathery.

Pedicel: Strong and glabrous, generally angled about 45° from vertical.

*Color.*—Forest Green on bottom side and Maroon on the top side.

*Length.*—4 to 5 inches.

THE FLOWER

Blooming habit: Annually, blooming profusely in late July.

Size: Large, averaging 7 to 9 inches in diameter.

Borne: From larger bulbs, the inflorescence has a raceme arrangement with each pedicel bearing one bud. The size of the bulb and its cultural care will determine the number of blooms and buds to be found on any given inflorescence. From large bulbs, this lily may have three to six blooms open at one time.

Shape: Flat, with uniformly spaced petals in star arrangement, with the very tips of the petals folding and curving backwardly.

Petalage: Normal, three sepals and three petals.

*Form.*—Oval, with cuspidate apex and sinuate edges.

*Size.*—About 5½ inches long and 3 inches wide.

*Color.*—Upper side: Upon opening, the midrib of the petal is Red Purple RHS 60A fading to RHS 70D for the remainder of the petal. The entire petal area, excluding the tips, is profusely covered with Dark Maroon oblong spots. Under side: Greyed Purple RHS 186D and glabrous.

*Papillae.*—Present on the petals, and from 4 to 8 in number.

*Texture.*—Leathery.

*Aspect.*—Velvety.

Fragrance: Sweet.

Discoloration: The color darkens somewhat as the bloom matures.

Effect of weather: Generally the flower is not affected by wet weather, but the flower ages as temperature rises.

Persistence: The petals fall off the flower as it ages.

Lasting quality:

*On the plant.*—Two to three weeks depending upon the size of the bulb and environmental temperature.

*As a cut flower.*—Ten days to two weeks.

REPRODUCTIVE ORGANS

Stamens:

*Number.*—Six.

*Anthers.*—About 1¼ inches long and orderly arranged around the pistil.

*Filaments.*—Length — about 3 inches.

*Color.*—Greenish Yellow.

Pistils:

*Number.*—One.

*Style.*—Length — about 4 inches. Color: Light Green at the base, darkening somewhat at the stigma.

*Stigma.*—Light Grey in color.

Ovary: Classified as a schizocarp, about 3 inches long and 2 inches in diameter, dehiscing into thirds and containing six rows of seeds of the usual shape for lilies.

I claim:

1. A new and distinct variety of Oriental Hybrid lily plant substantially as herein shown and described, characterized by its very large, brilliantly colored flowers borne on strong, stiff, upwardly-projecting pedicels, by its short and compact pot growth habit, and by its dark green, glossy foliage.

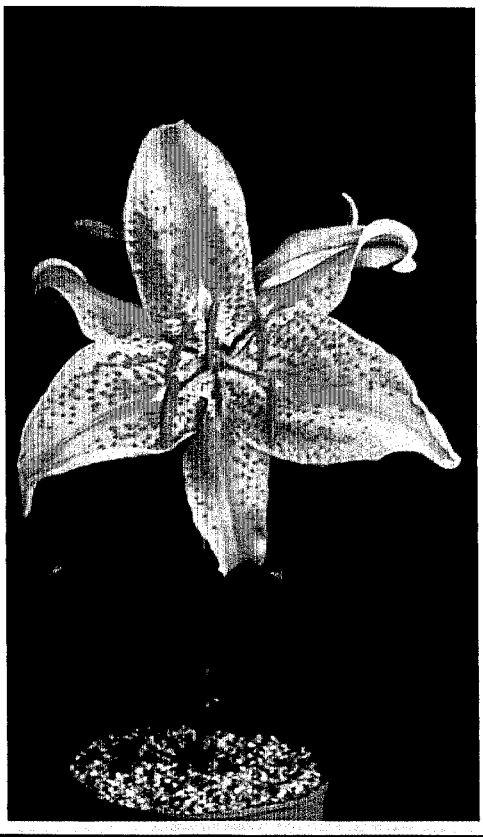
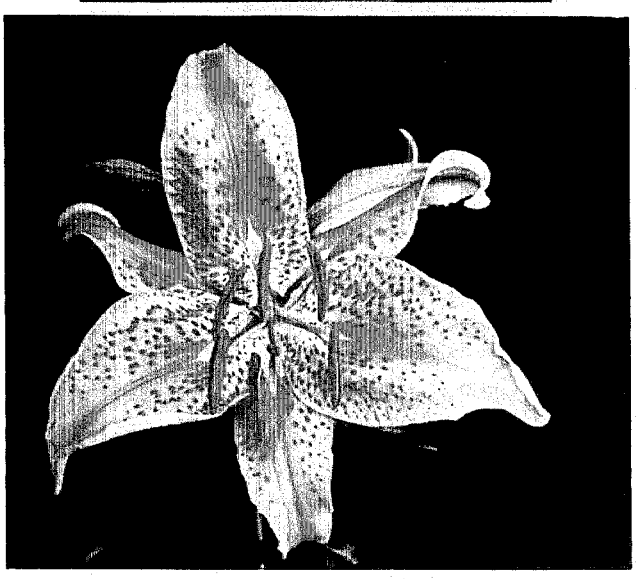

* * * * *